US008566727B2

(12) United States Patent
Mahesh et al.

(10) Patent No.: US 8,566,727 B2
(45) Date of Patent: Oct. 22, 2013

(54) METHOD AND SYSTEM FOR AUTOMATING A USER INTERFACE

(75) Inventors: Prakash Mahesh, Hoffman Estates, IL (US); Murali Kariathungal, Hoffman Estates, IL (US); Mark Morita, Arlington Heights, IL (US)

(73) Assignee: General Electric Company, Schenectady, NY (US)

(*) Notice: Subject to any disclaimer, the term of this patent is extended or adjusted under 35 U.S.C. 154(b) by 336 days.

(21) Appl. No.: 11/619,432

(22) Filed: Jan. 3, 2007

(65) Prior Publication Data

US 2008/0163070 A1     Jul. 3, 2008

(51) Int. Cl.
*G06F 3/00* (2006.01)
*G06F 3/048* (2013.01)

(52) U.S. Cl.
USPC ............................................ 715/744; 715/733

(58) Field of Classification Search
USPC .......................................... 715/733, 744, 747
See application file for complete search history.

(56) References Cited

U.S. PATENT DOCUMENTS

| | | | |
|---|---|---|---|
| 5,414,811 A | | 5/1995 | Parulski et al. |
| 5,878,746 A | * | 3/1999 | Lemelson et al. ............ 600/407 |
| 6,173,275 B1 | | 1/2001 | Caid et al. |
| 6,411,836 B1 | * | 6/2002 | Patel et al. .................... 600/407 |
| 6,760,714 B1 | | 7/2004 | Caid et al. |
| 7,283,857 B1 | * | 10/2007 | Fallon et al. ................. 600/407 |
| 7,617,078 B2 | * | 11/2009 | Rao et al. ........................ 703/2 |
| 2003/0120458 A1 | * | 6/2003 | Rao et al. ..................... 702/181 |
| 2005/0102315 A1 | * | 5/2005 | Krishnan ..................... 707/102 |
| 2005/0148861 A1 | * | 7/2005 | Ramanathan et al. ........ 600/410 |
| 2005/0267351 A1 | * | 12/2005 | Humphrey et al. ........... 600/408 |
| 2006/0242638 A1 | * | 10/2006 | Lew et al. ..................... 717/168 |
| 2006/0247863 A1 | * | 11/2006 | Bui ................................ 702/19 |
| 2006/0248474 A1 | * | 11/2006 | Kimotsuki .................... 715/810 |
| 2007/0054350 A1 | * | 3/2007 | Walker, Jr. ..................... 435/34 |
| 2007/0064981 A1 | * | 3/2007 | Meijer .......................... 382/128 |
| 2008/0109250 A1 | * | 5/2008 | Walker et al. .................... 705/2 |
| 2009/0324097 A1 | * | 12/2009 | Ramsay et al. ............... 382/209 |

* cited by examiner

*Primary Examiner* — Rashawn Tillery
(74) *Attorney, Agent, or Firm* — Hanley, Flight and Zimmerman, LLC

(57) ABSTRACT

Certain embodiments relate to providing automated, custom displays of images and tools for manipulating the images. Certain embodiments include a method for providing an automated user interface for healthcare workers. Certain embodiments of the method employ a network to execute the steps of retrieving an image from an image archive, processing the image to generate image-specific information, identifying data related to the image, mining the data related to the image, and displaying the image along with a custom selection of user interface tools.

20 Claims, 2 Drawing Sheets

METHOD AND SYSTEM FOR AUTOMATING A USER INTERFACE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present method and system relate generally to electronic data collection and display in a healthcare setting. Particularly, certain embodiments relate to providing automated, custom displays of images and tools for manipulating the images.

Healthcare facilities often employ certain types of digital diagnostic imaging modalities, such as computed tomography, magnetic resonance imaging, ultrasound imaging, and X-ray imaging. As part of the therapeutic or diagnostic process, healthcare workers spend a considerable amount of time evaluating and interpreting images, as well as preparing clinical reports. The clinical reports often contain direct references to images as well as data gathered from the images.

To facilitate the evaluation and interpretation of images, computer-based systems have been developed to present the data to a user, typically a radiologist but possibly any of a number of other users in a healthcare setting. As with most computer-based systems, the user interacts with the system via input devices such as a mouse and/or a keyboard. Users who spend considerable time with such devices may develop conditions, such as carpal tunnel syndrome, common to computer-intensive workplaces. This is in part due to the reliance on input devices such as a mouse and/or a keyboard to perform what are often repetitive tasks.

Moreover, some of the analysis performed on images by users is predictable. Past images and past clinical reports related to a given patient may contain information that is helpful in determining what part or parts of a current image may be of interest to a user. In this way, certain parts of image analysis may be amenable to automation. A reliable way of automating image analysis based on past clinical data and past images could enable users to interpret and evaluate images more efficiently.

Thus, there is a need for a system and method to reduce the reliance on user input devices to perform the repetitive evaluation and analysis of images. There is a further need for a means of automating the predictable aspects of image interpretation and analysis.

BRIEF SUMMARY OF THE INVENTION

Certain embodiments of the present invention include a method for providing an automated user interface for healthcare workers interacting with an image analysis system. Certain embodiments of the method include the steps of retrieving an image from an image archive, processing the image to generate image-specific information, identifying data related to the image, mining the data related to the image, and displaying the image along with a custom selection of user interface tools.

Certain embodiments of the present invention include an automated user interface for use in a healthcare setting. According to certain embodiments, the automated user interface comprises a network, an image archive connected to the network, a data archive connected to the network, and a workstation connected to the network. According to certain embodiments, the workstation has a user interface device, image display capabilities, and user interface tools. According to certain embodiments, a rules engine is connected to the network, wherein the rules engine processes an archived image for display, identifies and mines archived data related to the archived image, and displays the image via the workstation along with a custom selection of user interface tools.

Figure 1:
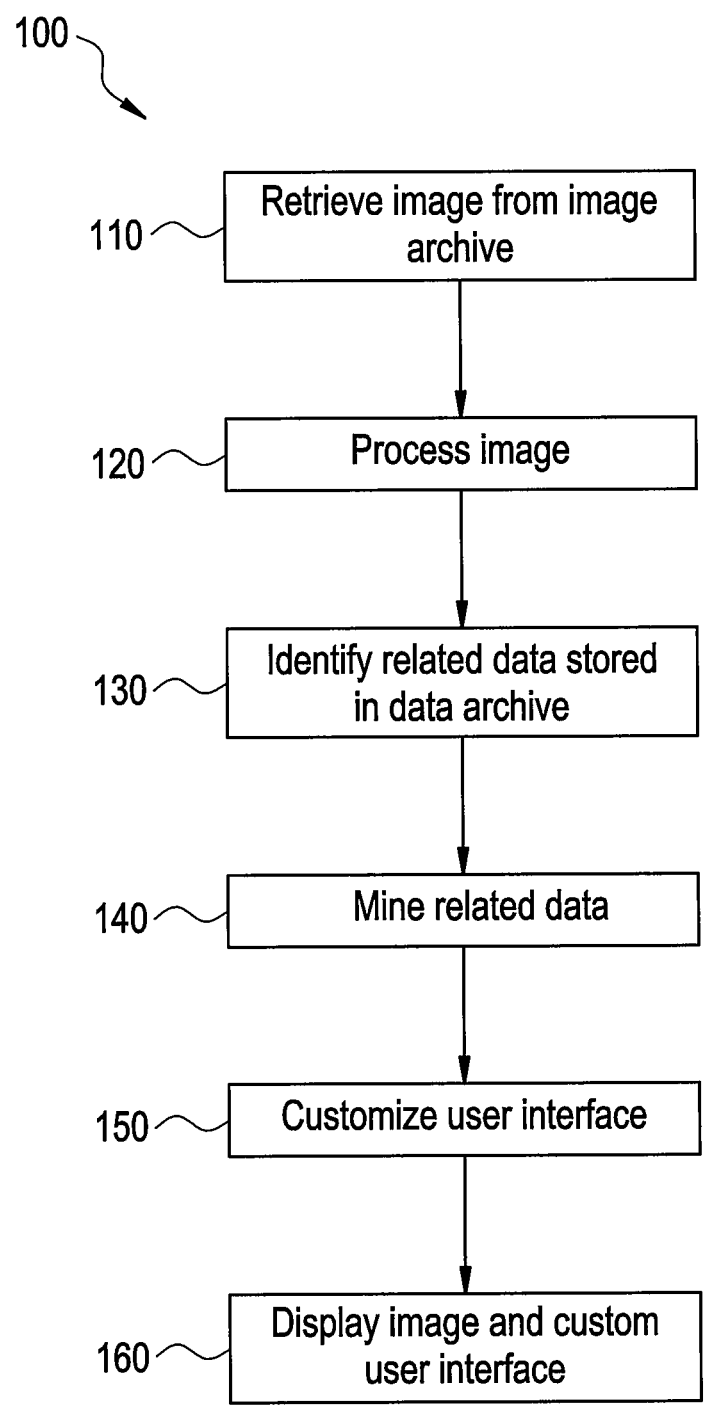
FIG. 1 illustrates a flow diagram for a method for automatically providing a custom user interface along with an image or images in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentalities shown in the attached drawings.

DETAILED DESCRIPTION OF THE INVENTION

The methods and systems of certain embodiments of the present invention contemplate that a user, typically a radiologist but potentially any healthcare worker or clinician, has an interest in viewing and analyzing images and data collected during diagnostic or therapeutic treatment of a subject. To this end, the user interfaces with a computerized image and data display system, typically through the use of a workstation. The workstation may be a standalone system or it may be a networked system. In the case of a networked system, the network may extend within a single healthcare facility or it may extend across multiple healthcare facilities. The networked system may be integrated with other networked systems, including networks carrying data other than images, for example, a network carrying patient demographic data. In any case, the user has access to stored images and stored data at least via the workstation.

Thus, in certain embodiments of methods and systems of the present invention the user interacts with a workstation to view and analyze specific images or series of images to further the diagnosis or treatment of a subject. Computerized image analysis and image manipulation tools facilitate image analysis by the user on the workstation. Such tools form part of the user interface of the workstation. Certain embodiment of the methods and systems of the present invention provide an automated and customizable user interface.

FIG. 1 illustrates a flow diagram for a method 100 for automatically providing a custom user interface along with an image or images in accordance with an embodiment of the present invention. In retrieval step 110 of method 100, an image or images are retrieved from an image archive. Typically, retrieval step 110 takes place in response to a user's request to a view an image associated with a specific patient. Retrieval step 110 may involve retrieving a single image, or it may involve retrieving a series of images.

In the case of a series of images, the series may be images collected during a single patient imaging event, such as a series of "image slices" captured during a computerized-tomography imaging session. Of course, other imaging modalities capable of producing a series of images or having their images collected in a series are also contemplated by this embodiment. In addition, the series of images may be images collected during different imaging events. The images may have been previously associated with each other by a clinician to form a series. Or, the images may be currently associated with each other to form a series by the clinician during retrieval step 110. For example, the request data input from the user may contain multiple image requests, thus potentially associated the images.

The image archive from which the image is retrieved in step 110 may be an archive local to the workstation or it may be from a networked data archive. The workstation may be part of a Picture Archive and Communication System (PACS).

Referring again to FIG. 1, in image processing step 120 an image is processed to gather information relevant or helpful to the method of one embodiment of the present invention. Again, the image may be a single image or it may be a series of images. Image processing step 120 may include identifying the similarities and/or differences among features present in each image of a series of images. For example, in a series of "images slices" which recreate a three-dimensional section of a subject, differences among the images can be used to identify irregularities in the tissue being imaged. Similarly, images or series of images collected during different imaging sessions for a certain subject can be processed to identify similarities or differences among the images.

In any case, one object of image processing step 120 in one embodiment of the present invention is to identify image information of potential interest to the user. For example, in the case of a series of "images slices" which recreate a three-dimensional section of a subject, the presence of systematic differences in images features may indicate the presence of abnormal tissue growth. The presence of this abnormal growth is potentially of interest to the user and immediately viewing the portion of the image containing the abnormal growth can expedite a diagnosis of the subject's condition. Thus, image processing step 120 is useful at least to automate the collection of image-specific information to be displayed to the user as part of the customized user interface.

Moreover, while the above discussion highlights a processing methodology that seeks to compare images to find differences or similarities in image features, other image processing methodologies may be suitable for identifying information of potential interest to the user. Such other methodologies may include, for example, performing mathematical analysis of the images to generate information not readily apparent upon visual inspection of the image.

Another object of image processing step 120 in one embodiment of the present invention is to help customize the selection of tools presented to the user as part of the user interface. For example, in the above-mentioned case of the presence of systematic difference in images features that may indicate the presence of abnormal tissue growth, a user is likely to want to measure the growth as part of the diagnosis process. Immediately presenting the measurement tool as part of the custom user interface can expedite a diagnosis.

Thus, image processing step 120 is useful at least to customize the selection of user interface tools to be displayed to the user as part of the customized user interface.

Image processing step 120 may take place as part of a software routine available locally on the workstation. Alternatively, the image processing routine may be part of a software routine available on the image archive or on a network linking the archive and the workstation.

Referring again to FIG. 1, during data identifying step 130, data that is relevant or potentially relevant to a users diagnosis of a subjects condition is identified according to one embodiment of the present invention. In order to identify the relevant data, identifying step 130 may be aided through the use of data input. For example, patient demographic information may be helpful for data identifying step 130 to locate clinical reports or other data kept in a data archive and relevant to the diagnosis.

In the example where patient demographic information is used, such information may be provided directly by the user at the same time the user requests to a view an image as part of image retrieval step 110. In such a case, the user may directly request the retrieval of a specific clinical report or other data or sets of data stored on a data archive by inputting patient demographic data or other patient identifying data. With such a direct request from the user, patient demographic information may readily be extracted from the direct request and supplied as input to data identifying step 130. Data identifying step 130 may then use the patient demographic information input to identify other patient data potentially relevant for automatically providing a customized user interface. Examples of potentially relevant data include other clinical reports for the subject available in a data archive but not specifically requested by the user. Further examples of potentially relevant data include patient specific data stored on other data archives networked with the workstation. Data identifying step 130 may optionally also perform the task of retrieving the specific data requested by the user.

In other examples related to providing input to data identifying step 130 according to one embodiment of the present invention, the user may indirectly provide input useful for identifying related data. For example, a user may simply request an image or series of images but not also request the retrieval of a related clinical report. In such case, data identifying step 130 may evaluate data or meta-data associated with the requested image to provide the input potentially necessary to identify data related to the requested image. As described above, many current imaging system use data objects associated with images in the DICOM format. Thus, data identifying step 130 may evaluate the DICOM data objects associated with a requested image and use certain data objects as keys for further data identification. DICOM data objects may include, for example, patient demographic information. Once such patient demographic information is obtained, data identifying step 130 can proceed as outlined above to locate potentially relevant data useful for automatically customizing a user interface. Additionally, images may be associated with each other as a result of data identifying step 130, according to one embodiment of the present invention. For example, the DICOM data objects may include information relevant for identifying other images in the image archive that can be processed according to image processing step 120 to yield further opportunities to customizing or refining the customization of the user interface.

Referring again to FIG. 1, in data mining step 140, data identified through data identifying step 130 is evaluated to facilitate the automated customization of a user interface, according to one embodiment of the present invention. In such an embodiment, data mining step 140 involves scanning the identified data for text or other data that are potentially relevant for customizing the user interface. Text and data can be identified as relevant following at least a few different processes.

According to one embodiment of the present invention, the data mining of data mining step 140 may occur with a set of pre-determined rules. Pre-determined rules relate to patterns of data known to occur or known to be likely to occur in a given data set. Such data patterns may involve small or large pieces of an individual data set. The data patterns may also occur across individual data sets, such as a series of clinical reports.

One example of a pre-determined rule involves a data pattern having a numerical entry followed by text typically known to connote a unit of measure, such as "14 mm," which could be referred to as a measurement rule. The presence of such a measurement rule may indicate, for example, a previous identification and diagnosis of a tissue abnormality. The presence of the measurement rule may then trigger a search in the nearby data for a second level of pre-determined rules common to the diagnosis of a tissue abnormality, such as for example the text string "nodule." Many other second level pre-determined rules are possible and are within the scope of data mining step 140. Further, data mining step 140 may involve nesting the pre-determined rules described above in a different order such that data mining step 140 searches first for the text string "nodule" and the measurement rule is a second tier rule. Of course, the nesting of rules is not limited to two levels and can have many levels. Moreover, searches for different pre-determined rules may occur in parallel in the same data set and may also occur recursively in a given data set.

According to one embodiment of the present invention, data mining step 140 may generate learned rules. Learned rules involve data patterns that emerge from a data set as that data set is evaluated. As in the case of pre-determined rules, learned rules may emerge for large or small patterns of data and may extend across multiple data sets. Important data patterns are desirable for use as learned rules to facilitate execution of data mining step 140. The importance of a data pattern is determined at least in part by several factors, including the data pattern's frequency, proximity to other key data, and the relevance of the data contained within the pattern.

Frequently occurring data patterns may be important in a given data set as a means of determining the identity of data that has been of interest to a user. A frequent text string such as "fibrous mass" may indicate that such tissue abnormality has been the subject of past user interest. Conversely, a single occurrence of the text string "fibrous mass" in a large data set may indicate that such tissue abnormality has been identified in the past and is not of interest. As with the above example of a second level of search using predetermined rule after locating a first pre-determined rule, a second level of search, and multiple further levels of search, can be used to refine the importance of an emerging data pattern.

In one embodiment of the present invention, data mining step 140 may use only pre-determined rules, or it may use only learned rules. Preferably, data mining step 140 uses a combination of pre-determined rules and learned rules to locate potentially relevant data useful for automatically customizing a user interface. Further, a learned rule may be added to the set of pre-determined rules available for data mining. The added learned rule may be added in a specific form, such as for example the text string "fibrous mass," or it may be added in a more generic form aids in identifying patterns that deviate somewhat from the specific learned rule.

In one embodiment of the present invention, pre-determined rules used in data mining step 140 may come from data or meta-data evaluated during data identifying step 130. For example, data identifying step 130 may evaluate the DICOM data objects associated with a requested image and use certain data objects as output for the formation of a pre-determined rule useful in data mining step 140. Thus, data identifying step 140 may provide content related to data mining step 140 in addition to locating relevant data.

Referring again to FIG. 1, in customizing step 150 the results of image processing step 120, data identifying step 130, and data mining step 140 may be used to customize the user interface, according to one embodiment of the present invention. In one embodiment, as custom user interface is one in which area or areas of interest in an image are highlighted for the user and useful user interface tools are presented to the user.

For example, as a result of image processing step 120, certain features such as tissue abnormalities may have been identified in an image or series of images. In one embodiment, customizing step 150 correlates the feature size and location on the image or series of images and selects an appropriate image size, image alignment, and/or image magnification to highlight the tissue abnormality for the user. In the event that image processing step 120 has identified multiple image features in an image or series of images, customizing step 150 may apply rules regarding the priority of display of such multiple features.

For example, if image processing step 120 has identified two features of interest to a user, such as a fibrous mass and a potential fluid sac, customizing step 150 may apply rules that indicate a priority for the potential fluid sac. Thus, customizing step 150 may select image orientation and magnification parameters that first highlight the fluid sac. Customizing step 150 may further select image orientation and magnification parameters that highlight the fibrous mass for later display to the user.

In one embodiment of the present invention in which customizing step 150 determines the priority of display for image features, key data identified during data mining step 140 may also be used to prioritize image features. For example, if data mining step 140 generates information from clinical reports that the size and shape of a certain image feature has been frequently measured, then that tissue feature may receive a high display priority since it appears to be of interest to a user. Customizing step 150 may also have rules to reconcile conflicting priorities. For example, when an otherwise low priority image feature has been frequently measured in past clinical reports, customizing step 150 may raise the display priority of such otherwise low priority image feature.

In one embodiment of the present invention, customizing step 150 may generate a list of user interface tools to be presented to a user along with the customized image orientation and magnification. For example, if image processing step 120 and/or data mining step 140 has identified an image feature of interest for measurement by a user, customizing step 150 may assign a high priority to the measurement tool. Further, in this example customizing step 150 may also assign a high priority to an annotation tool. Thus, customizing step 150 is useful for automatically customizing the user interface in that it may provide immediate access to interesting features in an image, displayed in a useful orientation and magnification, and may also provide immediate access to specific image manipulation tools.

Referring again to FIG. 1, in displaying step 160 the image or images retrieved from the archive may be displayed for the user following the custom parameters generated by customizing step 160, according to one embodiment of the present invention. Additionally, a custom selection of tools may be displayed for the user in displaying step 160. Optionally, data sets identified through data identifying step 130 may also be displayed for the user. Further, certain data strings may be highlighted or featured for the user as part of displaying step 160.

The steps described above are illustrated in FIG. 1 as occurring sequentially. However, in certain embodiments of the present invention, some or all of the steps described above may occur in parallel. Further, some of the steps described above may be collapsed into a single step according to certain embodiments of the present invention. Of course, modifications in the timing, order, or number of the steps of the method of the present invention are contemplated and are within the scope of certain embodiments of the method. Further, the steps of the method may be carried out repeatedly in a loop according to certain embodiments of the present invention. The method steps described above lay out a flexible architecture for achieving an automated, customizable user interface.

Within the steps of certain embodiments of the method of the present invention, certain rules or sets of rules may be necessary to carry out certain functions. For example, in one embodiment of the method of the present invention, data mining step 140 employs certain rules that identify data patterns in order to carry out the mining function. Similarly, according to one embodiment, customizing step 150 employs certain priority rules to carry out the customizing function. Such an assembly of rules may be referred to as a rules engine. A rules engine may contain rules unique to a single method step or multiple method steps, according to certain embodiments of the present invention. A rules engine may also contain rules common to multiple method steps, and may contain a nested set of rules. Rules may be applied to data in routines or subroutines.

Figure 2:
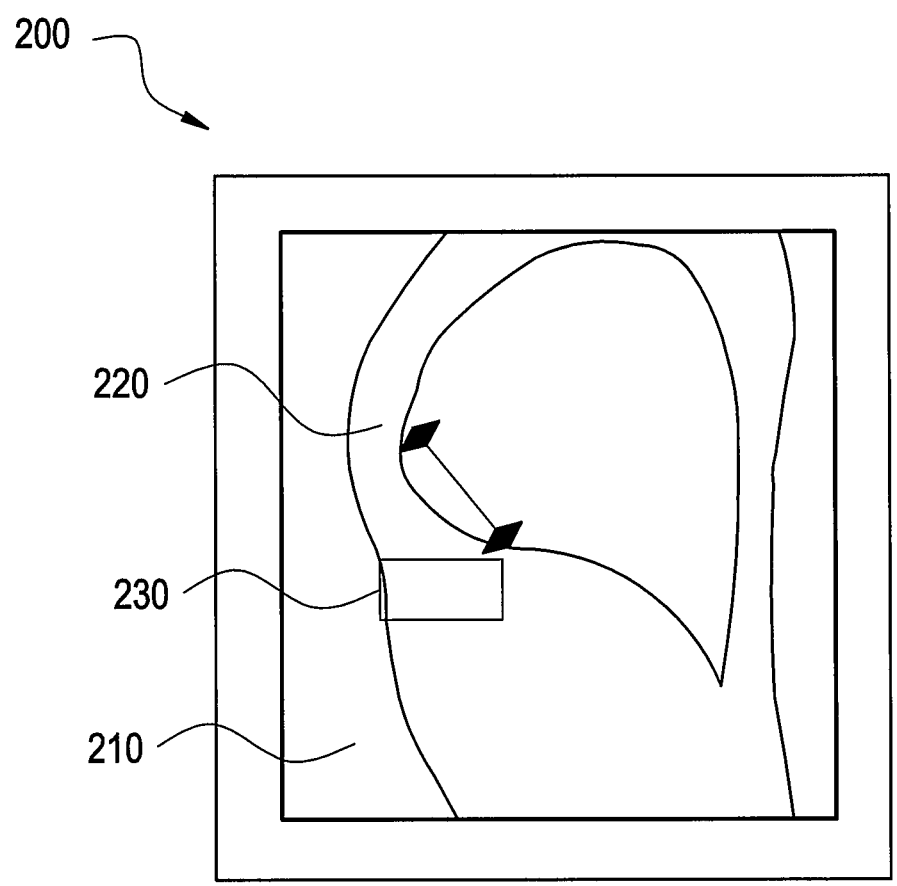
FIG. 2 illustrates a workstation display employing a customized user interface in accordance with an example of one embodiment of the present invention.

FIG. 2 illustrates a workstation display 200 employing a customized user interface in accordance with an example of one embodiment of the present invention. Workstation display 200 includes image 210, measurement tool 220, and annotation box 230, according to one embodiment of the present invention. FIG. 2 illustrates an example of a customized user interface, in that a specific image is displayed along with certain user interface tools. In this example, the selected user interface tools are measurement tool 220 and annotation box 230 as a result of the image processing and data mining of one embodiment of the present invention. Although only two user interface tools are depicted in FIG. 2, and number of user interface tools may be selected for immediate or sequential display. Example of user interface tools include panning, selecting a region of interest, annotation, and window leveling.

The methods of embodiments of the present invention may be executed using systems including a workstation, an image archive, and a data archive. In one embodiment, the workstation may be a standalone system with images and data archived on the workstation. Preferably, the workstation, image archive, and data archive are networked together. The network may include a plurality of workstations as well as multiple image archive and data archives, according to embodiments of the present invention.

According to certain embodiments, the workstation has a user interface device, image display capabilities, and user interface tools. According to certain embodiments, a rules engine is connected to the network, wherein the rules engine processes an archived image for display, identifies and mines archived data related to the archived image, and displays the image via the workstation along with a custom selection of user interface tools.

The technical effects of certain embodiments of the present method and system are to retrieve an image from an image archive, to process the image to generate image-specific information, to identify data related to the image, to mine the data related to the image, and to display the image along with a custom selection of user interface tools.

As described above, the methods of embodiments of the present invention may employ routines and subroutines to carry out certain method steps. The routines and subroutines may be stored on computer readable media accessible to a workstation according to one embodiment. Accessibility includes without limitation having the media stored within a workstation or stored on a network connected to a workstation. The routines and subroutines may be used to implement the rules or rules engines described above, in accordance with an embodiment of the present invention.

EXAMPLE

A radiologist in an academic/teaching hospital specializes in CT readings. So, the radiologist's workflow is normally going through a long worklist with CT exams. The radiologist's focus is both on quality and productivity. Under prior art conditions, the radiologist opens every exam, views the images, historical images, historical reports and then does image manipulation like zoom, windowlevel, pan to get the right quality of the images and then performs annotations, enters key image notes and then creates reports. This whole prior art process takes many minutes, repeating the process for every exam.

Using an embodiment of the present invention for patient X, the radiologist is assisted by providing some of patient X's information ahead of time. When the radiologist opens an exam—the image manipulation is done and needs just minor work. Regions of interest are marked and annotations are entered based on how he has been doing it, that is, the system learns based on past practice. So, it reduces the time it takes for the radiologist to read every exam.

One potential advantage of the system and method of the present invention is a reduced reliance on mouse and keyboard. Since the user is presented with a customized user interface tailored to the specific image and data displayed on the workstation, there is less of a need for the user to employ the mouse and keyboard to select appropriate user tools. This reduced reliance on a mouse and keyboard may in turn yield further advantages. For example, less reliance on a mouse and keyboard may lessen the incidence of carpal tunnel syndrome in users of the system and method of the present invention. Another potential advantage of the system and method of the present invention is that of focusing the limited time of a busy clinician on medically-oriented tasks rather than software-oriented tasks. This increased medical focus potentially provides a benefit to the user in that the user's time is occupied more efficiently. Moreover, it potentially provides a benefit to the subject in that the user is able to turn more attention to the interpretation and analysis of diagnostic data rather than spending time navigating software.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for providing an automated user interface for healthcare workers comprising:
performing by at least one processing device, at least:
automatically processing an image of a patient's anatomy to identify a feature of interest and generate image-specific information regarding the feature of interest;
using the generated image-specific information to identify data in an archive that is related to the image;
mining the identified data to automatically select, based on image content and the processing of the image, at least one user interface tool from a plurality of user interface tools that is to be used to manipulate the image; and
displaying a custom user interface including the image and the selected at least one user interface tool such that the displayed at least one user interface tool can be used to manipulate the displayed image.

2. The method of claim 1, further comprising using the patient's demographic information to identify data in the archive that is related to the image.

3. The method of claim 1, wherein the related data includes a previous imaging study image that includes the feature of interest.

4. The method of claim 1, wherein the at least one user interface tool selected by the mining was used to manipulate a previous imaging study image that includes the feature of interest.

5. The method of claim 1, wherein the displayed at least one user interface tool comprises at least one of: an annotation box, a zoom level tool, a measurement tool, a panning tool, a region of interest selection tool, and a window leveling tool.

6. The method of claim 1, further including:
mining the identified data to determine a display setting for the image; and
displaying the image using the display setting.

7. The method of claim 6, wherein the display setting determined by the mining was used to display a previous imaging study image that includes the feature of interest.

8. The method of claim 6, wherein the display setting comprises at least one of: an annotation, a zoom level, a panning setting, a measurement indicator, focus on a region of interest, and a window level.

9. The method of claim 1, wherein the at least one user interface tool comprises at least two user interface tools, and wherein the at least two user interface tools is displayed as a prioritized list, priority being determined based on frequency of use of the user interface tools in previous imaging studies that include the feature of interest.

10. A system for providing an automated user interface for healthcare workers comprising:
a computer processor in operable communication with an archive and a user interface,
the computer processor configured to automatically process an image of a patient's anatomy to identify a feature of interest and generate image-specific information regarding the feature of interest,
the computer processor configured to use the generated image-specific information to identify data in the archive that is related to the image;
the computer processor configured to mine the identified data to automatically select, based on image content and the processing of the image, at least one user interface tool from a plurality of user interface tools that can be used to manipulate the image; and
the user interface configured to display the image and the selected at least one user interface tool such that the displayed at least one user interface tool is to be used to manipulate the displayed image.

11. The system of claim 9, wherein the computer processor is configured to use the patient's demographic information to identify data in the archive that is related to the image.

12. The system of claim 9, wherein the related data includes a previous imaging study image that includes the feature of interest.

13. The system of claim 10, wherein the at least one user interface tool selected by mining was used to manipulate a previous imaging study image that includes the feature of interest.

14. The system of claim 10, wherein the displayed at least one user interface tool comprises at least one of: an annotation box, a zoom level tool, a measurement tool, a panning tool, a region of interest selection tool, and a window leveling tool.

15. The system of claim 10, wherein the computer processor is configured to mine the identified data to determine a display setting for the image, and the user interface is configured to display the image using the display setting.

16. The system of claim 15, wherein the display setting determined by mining was used to display a previous imaging study image that includes the feature of interest.

17. The system of claim 15, wherein the display setting comprises at least one of: an annotation, a zoom level, a panning setting, a measurement indicator, focus on a region of interest, and a window level.

18. The system of claim 10, wherein the at least one user interface tool comprises at least two user interface tools, and wherein the at least two user interface tools is displayed as a prioritized list, priority being determined based on frequency of use in previous imaging studies that include the feature of interest.

19. A non-transitory computer readable storage medium including a set of instructions for a computer, the set of instructions comprising:
a first routine configured to automatically process an image of a patient's anatomy to identify a feature of interest and generate image-specific information regarding the feature of interest,
a second routine configured to use the generated image-specific information to identify data in an archive that is related to the image;
a third routine configured to mine the identified data to automatically select, based on image content and the processing of the image, at least one user interface tool from a plurality of user interface tools that is to be used to manipulate the image; and
a fourth routine configured to display the image and the selected at least one user interface tool such that the displayed at least one user interface tool can be used to manipulate the displayed image.

20. The medium and instruction of claim 19, further comprising a fifth routine configured to mine the identified data to determine a display setting for the image, wherein the fourth routine is configured to display the image using the display setting.

* * * * *